(12) United States Patent
Tsujii (10) Patent No.: US 7,050,537 B2
(45) Date of Patent: May 23, 2006

(54) RADIOGRAPHIC APPARATUS, RADIOGRAPHIC METHOD, PROGRAM, COMPUTER-READABLE STORAGE MEDIUM, RADIOGRAPHIC SYSTEM, IMAGE DIAGNOSIS AIDING METHOD, AND IMAGE DIAGNOSIS AIDING SYSTEM

(75) Inventor: Osamu Tsujii, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/290,184

(22) Filed: Nov. 8, 2002

(65) Prior Publication Data

US 2003/0190010 A1    Oct. 9, 2003

(30) Foreign Application Priority Data

Apr. 3, 2002  (JP)  ............................. 2002-101206
Aug. 26, 2002  (JP)  ............................. 2002-245285

(51) Int. Cl.
*H05G 1/10* (2006.01)

(52) U.S. Cl. ........................................................ 378/95

(58) Field of Classification Search .................... 378/8, 378/95
See application file for complete search history.

(56) References Cited

U.S. PATENT DOCUMENTS

| 5,067,494 | A |  | 11/1991 | Rienmueller et al. | .... 128/653.1 |
| 5,764,723 | A |  | 6/1998 | Weinberger et al. | .......... 378/65 |
| 6,298,260 | B1 | * | 10/2001 | Sontag et al. | ............... 600/413 |
| 6,353,653 | B1 | * | 3/2002 | Edic | .............................. 378/8 |
| 6,644,851 | B1 | * | 11/2003 | Kumagai | ..................... 378/167 |
| 2001/0015407 | A1 |  | 8/2001 | Tsuji | ....................... 250/252.1 |

FOREIGN PATENT DOCUMENTS

WO    WO 99/43253    9/1999

* cited by examiner

*Primary Examiner*—Craig E. Church
*Assistant Examiner*—Jurie Yun
(74) *Attorney, Agent, or Firm*—Fitzpatrick, Cella, Harper & Scinto (57) ABSTRACT

A radiographic apparatus or system for imaging a dynamic state or process of an object such as a human body includes an indication unit for performing dynamic state guiding indication using a perceivable pattern corresponding to a dynamic state or motion to be engaged in by the patient, and an image acquisition unit for acquiring a plurality of radiographs of the human body. The resulting radiographs can be reviewed for diagnosis, and can be stored, either locally or at a remote location.

6 Claims, 10 Drawing Sheets

RADIOGRAPHIC APPARATUS, RADIOGRAPHIC METHOD, PROGRAM, COMPUTER-READABLE STORAGE MEDIUM, RADIOGRAPHIC SYSTEM, IMAGE DIAGNOSIS AIDING METHOD, AND IMAGE DIAGNOSIS AIDING SYSTEM

BACKGROUND OF THE INVENTION

1. Field of the Invention

The present invention relates to a radiographic apparatus, a radiographic method, a program, a computer-readable storage medium, a radiographic system, an image diagnosis aiding method, and an image diagnosis aiding system.

2. Description of the Related Art

In recent years, systems that employ large-area semiconductor image sensors to radiograph an object have been developed. Such a system has practical advantages, as compared with a conventional radiographic system based on silver salt films, in that an image can be recorded over an extremely large range of radiation dose. More specifically, X-rays with an extremely wide dynamic range are read as electric signals using a photoelectric converter, and the electric signals are converted into digital signals. The digital signals are processed to output a high-quality radiograph as a visible image on a recording material such as a photosensitive film material, or to a display apparatus such as a CRT display. Accordingly, an adequate radiograph is obtained even if the dose of radiation exposure fluctuates somewhat.

In radiography using semiconductor image sensors, dynamic imaging of the lung during breathing, instead of the conventional diagnostic imaging primarily based on still imaging, is expected to provide new pathologic information. The imaging of the lung during breathing is such that the lung is dynamically imaged from when it is expanded to when it is contracted, preferably for one cycle of breath including an expanding period and a contracting period of the lung.

In conventional still imaging, guidance for keeping a patient still (by which is meant, whatever is done toward keeping the patient still) has been performed not by a machine but by a technologist. This is because it is more difficult to achieve appropriate timing of exposure, using machine guidance.

In imaging of the lung during breathing, as opposed to still imaging of the lung with the breath held, it is difficult to acquire image data of a breathing cycle (breathing period) accurately in phase (e.g., to acquire image data from start of inhaling to end of exhaling) within dynamic images that are continuously captured. This is because even if a patient is instructed to start inhaling upon start of imaging, some amount of delay—an amount that depends on the patient—occurs. In particular, the delay is prominent in aged patients or patients with weakened physical strength since these patients are unable to respond quickly. When a doctor diagnoses images that have been thus taken, if the phase of breathing at start of image display differs from patient to patient, a diagnosis method cannot be fixed and diagnosis will take more time.

This variation in phase at the start of image display can be reduced by controlling timing of the start and end of imaging, using a sensor for monitoring breath. However, this requires an instrument to be attached to a patient, which adds labor and time to the procedure. Furthermore, when imaging is performed over a breathing cycle, including inhaling and exhaling, during approximately ten seconds, it is difficult for a technologist suitably to control an inhaling phase and an exhaling phase to be five seconds each while monitoring the patient. Accordingly, it was necessary to guide a breathing cycle of the patient and to control imaging (e.g., X-ray irradiation) in accordance with the guide.

SUMMARY OF THE INVENTION

Accordingly, it is an object of the present invention to solve the problems described above.

To this end, the present invention, in one aspect thereof, provides a radiographic apparatus for imaging a dynamic state of a human body, including a first indication unit adapted to provide dynamic state guiding indication using a perceivable pattern which is repeated with a predetermined timing; and an image acquisition unit adapted to pick up the human body over a period of time to acquire a plurality of pieces of image data; a control unit adapted to synchronize acquisition of a piece of image data by said image acquisition unit with the time period; a storage unit adapted to relate phase information of the repeatedly presented perceivable pattern to the plurality of pieces of image data and to store the phase information; a phase analysis unit adapted to calculate phase information of the plurality of pieces of image data based on a geometrical feature value of the plurality of pieces of image data; a determination unit adapted to determine consistency between the calculated phase information and the stored phase information; a modification unit adapted to modify the stored phase information related to the image data into the calculated phase information; and a second indication unit adapted to indicate the plurality of pieces of image data based on the phase information with the predetermined timing, wherein, in a case in which said determination unit determines that the consistency is not appropriate the phase information related to the image data and stored in said storage unit is modified into the calculated phase information.

The present invention, in another aspect thereof, provides a radiographic method of imaging dynamic state of a human body by a radiographic apparatus, including an image acquisition unit adapted to acquire a radiograph, the radiographic method including a first indication step, of providing a dynamic state guiding indication using a perceivable pattern which is repeated with a predetermined timing; and an image acquisition step for picking up the human body over a period of time acquiring a plurality of pieces of image data; a control step for synchronizing acquisition of a piece of image data in said image acquisition step with the time period; a storage step, for relating phase information of the repeatedly presented perceivable pattern to the plurality of pieces of image data and for storing the phase information; a phase analysis step, for calculating phase information of the plurality of pieces of image data based on a geometrical feature value of the plurality of pieces of image data, a determination step, for determining consistency between the calculated phase information and the stored phase information; a modifying step, for modifying the stored phase information related to the image data into the calculated phase information; and a second indication step, for indicating the plurality of pieces of image data based on the phase information with the predetermined timing wherein, in a case in which it is determined in said determination step that the consistency is not appropriate, the stored phase information related to the image data is modified into the calculated phase information.

The present invention, in another aspect thereof, provides a computer-readable storage medium storing a program for having a computer execute a method of imaging a dynamic state of a human body by a radiographic apparatus including an image acquisition unit for acquiring a radiograph, the method including a first indication step, of providing dynamic state guiding indication using a perceivable pattern which is repeated with a predetermined timing; and an image acquisition step for picking up the human body over a period of time acquiring a plurality of pieces of image data; a control step for synchronizing acquisition of a piece of image data in said image acquisition step with the time period; a storage step, for relating phase information of the repeatedly presented perceivable pattern to the plurality of pieces of image data and for storing the phase information; a phase analysis step, for calculating phase information of the plurality of pieces of image data based on a geometrical feature value of the plurality of pieces of image data; a determination step, for determining consistency between the calculated phase information and the stored phase information; a modifying step, for modifying the stored phase information related to the image data into the calculated phase information; and a second indication step, for indicating the plurality of pieces of image data based on the phase information with the predetermined timing, wherein, in a case in which it is determined in said determination step that the consistency is not appropriate, the stored phase information related to the image data is modified into the calculated phase information.

Further objects, features and advantages of the present invention will become apparent from the following description of the preferred embodiments with reference to the attached drawings.

BRIEF DESCRIPTION OF THE DRAWINGS

The accompanying drawings, which are incorporated in and constitute a part of the specification, illustrate embodiments of the invention and, together with the descriptions, serve to explain the principle of the invention.

DESCRIPTION OF THE PREFERRED EMBODIMENTS

Preferred embodiments of the present invention will now be described in detail with reference to the accompanying drawings.

First Embodiment

Figure 1:
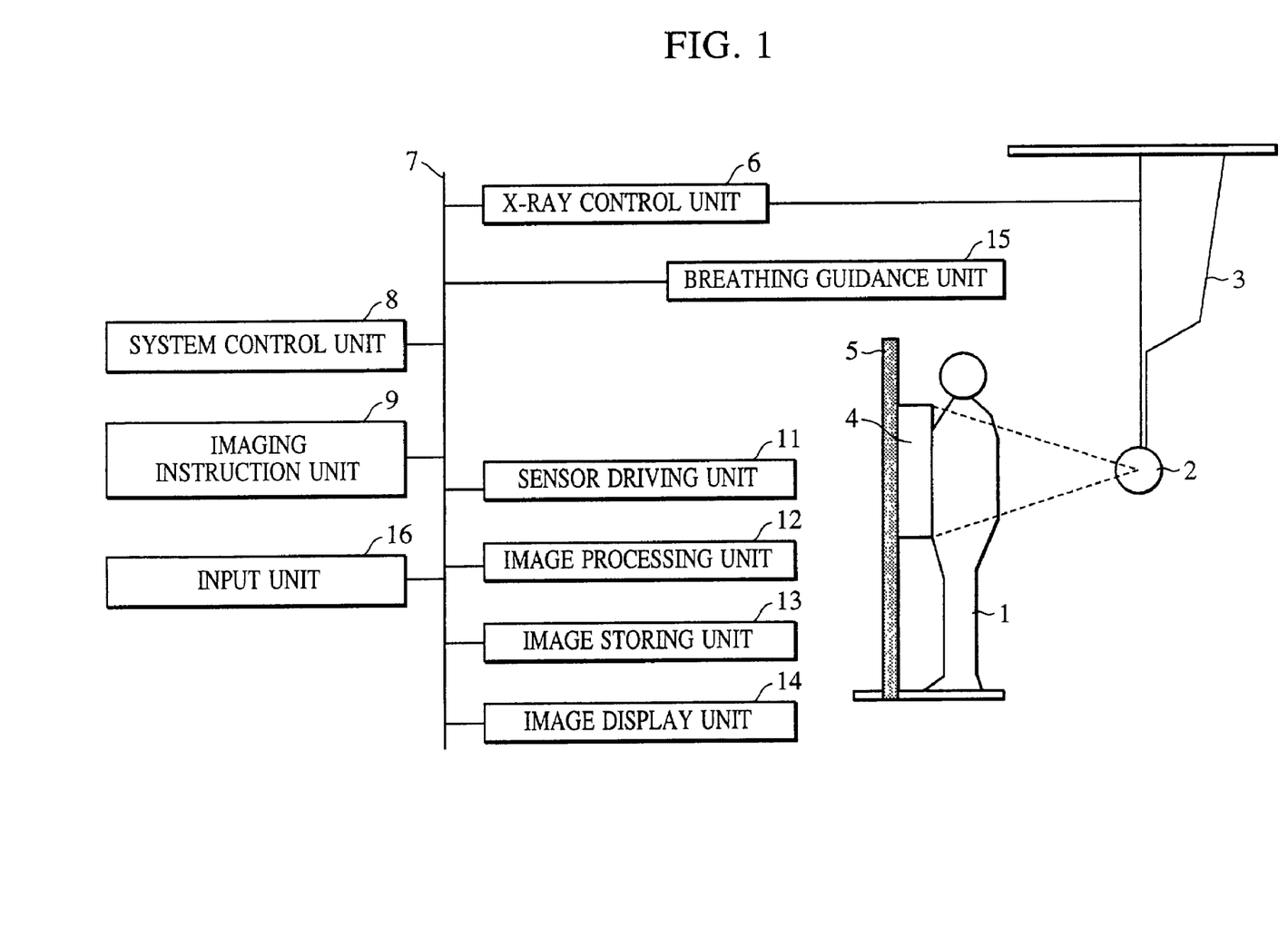
FIG. 1 is a system configuration diagram of a radiographic system according to an embodiment of the present invention.

FIG. 1 shows the construction of a system according to a first embodiment of the present invention. Referring to FIG. 1, a two-dimensional sensor 4, constituting an imaging unit, includes an amorphous semiconductor and a fluorescent screen, and it has 2,688×2,688 pixels each with a size of 160 $\mu m \times 160 \mu m$. The sensor 4 is attached to a stand 5 and is used for imaging an object in an upright position.

An X-ray tube 2 is suspended from a ceiling by a ceiling suspension unit 3 so as to be movable in accordance with the body of a patient (also referred to as a human body). X-rays produced by the X-ray tube 2 are transmitted through the patient to reach the sensor 4. The X-rays are converted into visible light by the fluorescent screen, and the visible light is converted into image data by the amorphous semiconductor. Timing of imaging is controlled based on instruction(s) entered from an imaging instruction unit 9 by a radiographic technologist (operator) or the like. Based on the instruction(s), a system controller 8 controls an X-ray control unit 6 and a sensor driving unit 11 to acquire an X-ray image.

A breathing cycle of a patient includes a period of inhaling mode and a period of exhaling mode. In inhaling mode, the patient inhales, increasing the pulmonary region of the chest accordingly and lowering the diaphragm. In exhaling mode, the patient exhales, decreasing the pulmonary region accordingly and raising the diaphragm.

A breathing cycle is defined as a cycle of respiration including one period of inhaling mode and one period of exhaling mode. For the purpose of observing respiration dynamically, an imaging time span of approximately ten seconds in total, including five seconds of inhaling mode and five seconds of exhaling mode, is considered as adequate. In this embodiment, an X-ray pulse is transmitted three times a second. An image is captured for each X-ray pulse, so that thirty images are obtained. The dose of radiation of a single X-ray pulse in dynamic radiography is approximately one tenth of that in ordinary still radiography. Thus, the dose of radiation for dynamic radiographs in this embodiment is equivalent to that for three still radiographs.

Now, a sequence of imaging will be described with reference to FIG. 2. The patient is positioned at the front of the sensor 4 by a technologist. The technologist inputs information that is to be attached to an image to be taken, such as patient information, via a user interface unit that is not shown, and then selects a mode for starting dynamic radiography of the patient's respiratory dynamic state.

The technologist reconfirms that the patient is ready, and then presses an imaging start request button provided on the imaging instruction unit 9. Based on a signal from the imaging start request button, guidance for breathing (indication output for guiding the patient's breathing) is started. For example, as shown in FIG. 2, at least one of audio output and visual display of a combination of "breathe in" and "breathe out" or the like is periodically performed.

The patient is expected to inhale and exhale in a breathing cycle in accordance with the breathing guidance. When the technologist confirms that the patient is breathing in a breathing cycle in accordance with the breathing guidance, the technologist presses a radiation exposure request button provided on the imaging instruction unit 9. Radiation exposure is now started, but not immediately after the radiation exposure request button is pressed. In the case of the example shown in FIG. 2, radiation exposure is started when the guidance for inhaling mode is started.

Figure 2:
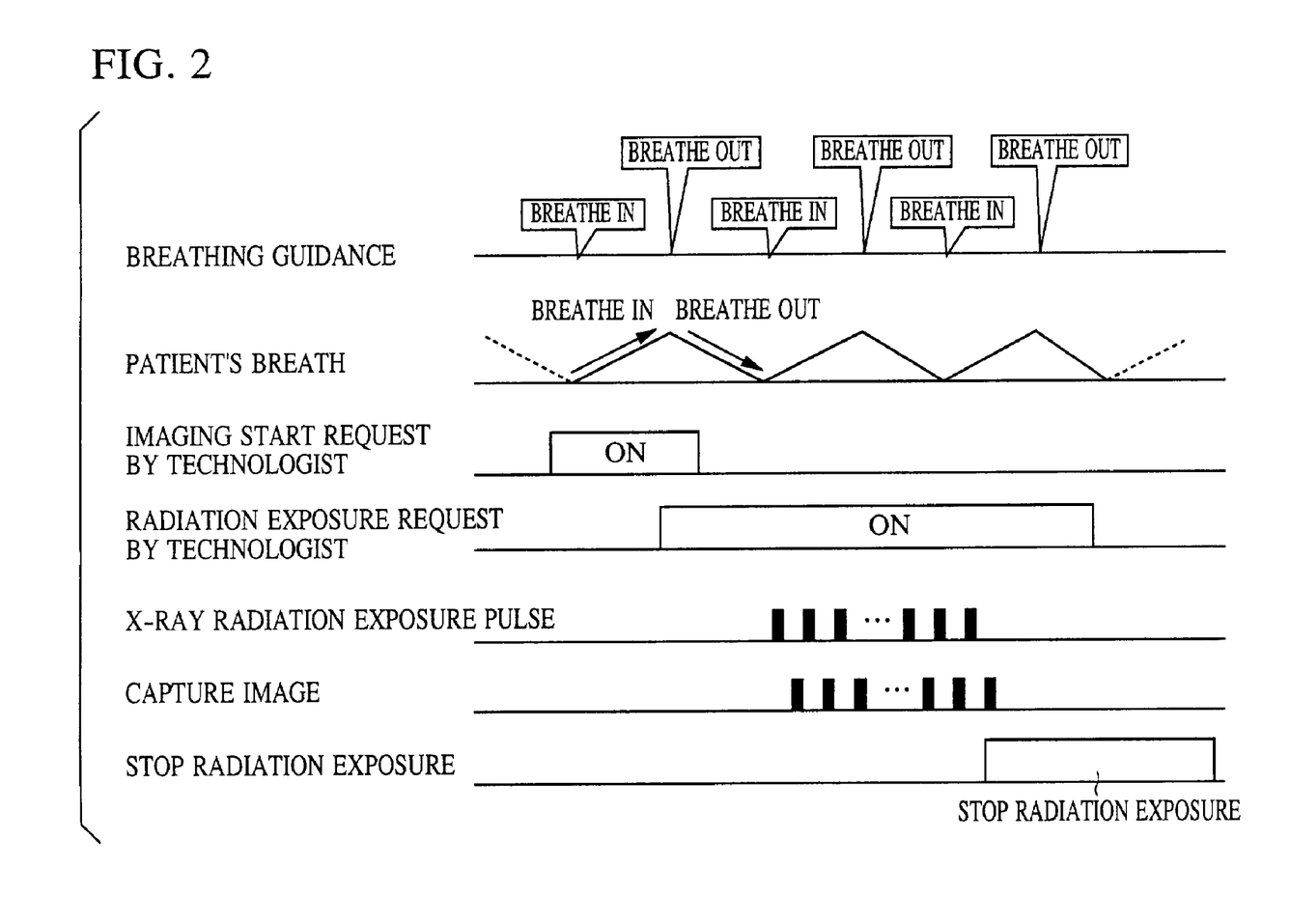
FIG. 2 is a timing chart of breathing guidance and imaging.

Although radiation exposure is started in the inhaling mode in the example shown in FIG. 2, alternatively, radiation exposure may be started in the exhaling mode. X-ray pulses are radiated thirty times in total, including fifteen times in five seconds of the inhaling mode and fifteen in five seconds of the exhaling mode, as described earlier. When the thirty times of radiation exposure are completed, X-ray radiation exposure is stopped, irrespective of the state of the radiation exposure request button operated by the technologist, in order to avoid unnecessary radiation exposure.

Although the duration of the inhaling and exhaling modes is five seconds each and the number of radiographs taken in one second is three in this embodiment, this embodiment is not limited to these values; preferably, these values may be modified via a user interface that is not shown.

Upon completion of each X-ray radiation exposure, an image is captured under the control of the sensor driving unit 11. Completion of X-ray radiation exposure may be detected based on a signal from the X-ray control unit 6 or based on a signal output from an X-ray monitor (not shown) incorporated in the sensor 4.

The breathing guidance by the breathing guidance unit 15 in the five seconds of the inhaling mode and in the five seconds of the exhaling mode may be performed by audio indication or visual indication, as mentioned earlier. In the case of audio indication, several phrases that express volumes of the lung are used in turn during the five seconds of the inhaling mode, for example, "start breathing in", "breathe in more deeply", "breathe in still more deeply", and "hold breath". Similarly, during the five seconds of the exhaling mode, several phrases are used in turn as appropriate, for example, "start breathing out", "breathe out slowly", "breathe out more", and "hold".

Figure 3:
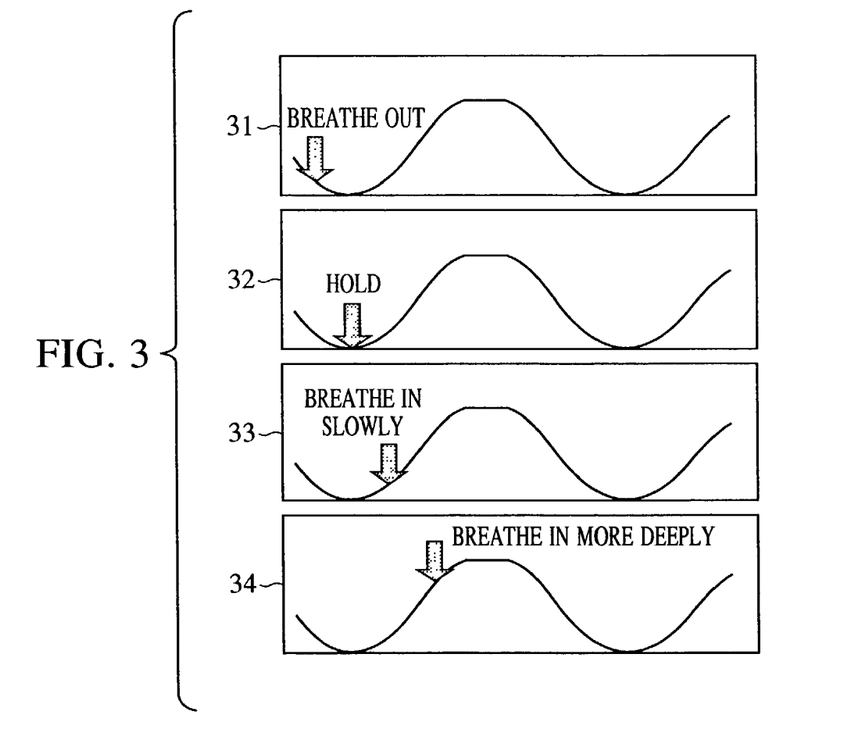
FIG. 3 is a diagram showing an example of indication by a breathing guidance unit.

In the case of visual indication, for example, visible characters corresponding to the phrases used in the audio indication as described above may be displayed, or alternatively, a graphical representation, such as a pattern representing the volume of the lung, such as a waveform (a sine wave, etc.) or the like, may be displayed, an example of which is shown in FIG. 3. Screens indicated as 31, 32, 33, and 34 represent respective display screens changing with time. The waveforms serve to let the patient be conscious of the volume of the lungs, and the arrows indicate current positions corresponding to volume of the lungs. Furthermore, phrases may be additionally displayed along with these indications, and the displayed phrases may be further indicated by audio. The indication of the waveform, messages, or the like is modified in accordance with time settings of the inhaling and exhaling modes described earlier. The time to be set for each mode is optimally equal to or longer than five seconds for observation of the dynamic state of the patient's respiration.

Figure 10:
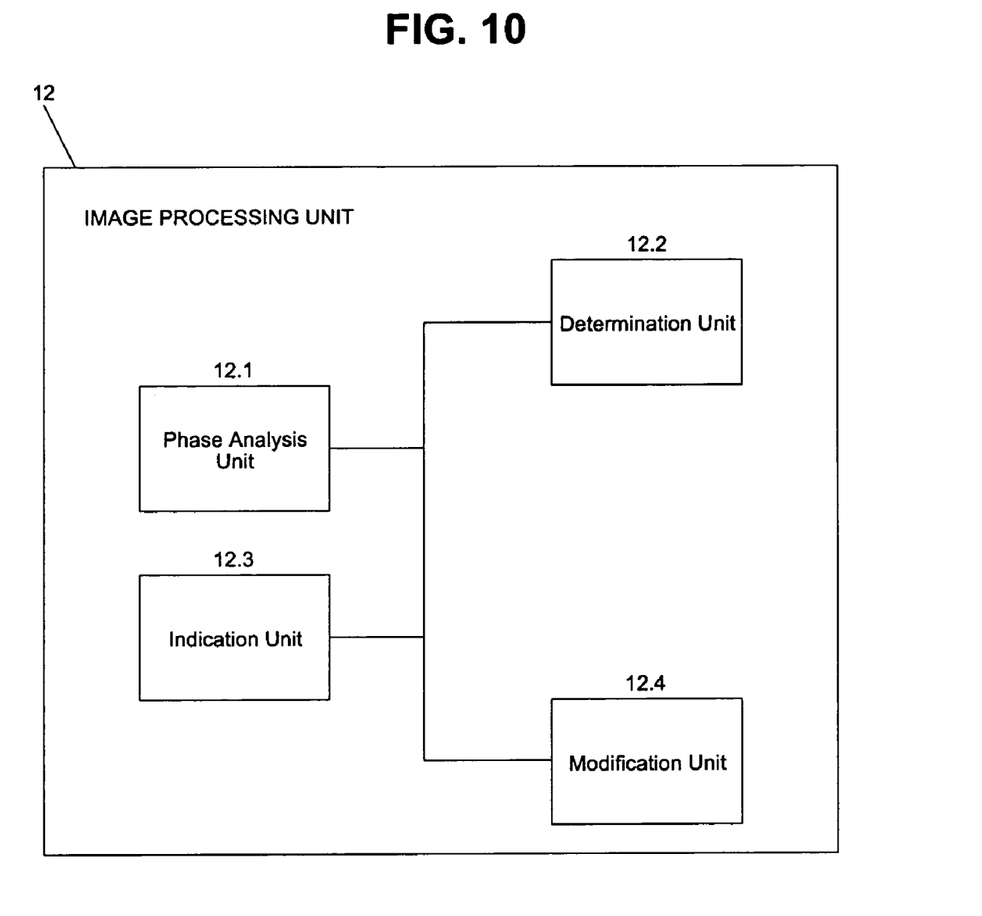
FIG. 10 is a block diagram of an image processing unit according to an embodiment of the present invention.

The images that have been taken are transferred to an image processing unit 12 via the sensor driving unit 11. The image processing unit executes a pre-process for correcting the images in accordance with characteristics of the sensor 4, a QA process for providing an image suitable for diagnosis by a doctor, and so forth. The pre-process includes offset correction, gain correction and defective pixel correction, etc. The QA process includes a sharpening process, a gray scale conversion process, etc. The images that have been processed by the image processing unit 12 are stored in an image storage unit 13. The image processing unit 12, which includes a phase analysis unit 12.1, a determination unit 12.2, an indication unit 12.3, and a modification unit 12.4 (shown in FIG. 10), is implemented by a computer, and the image storage unit 13 is implemented by a memory or magnetic disk of the computer.

The images that have been stored are sequentially displayed dynamically by an image display unit 14 based on instructions from an instruction unit (not shown) operated by an operator. The units that have been described hereinabove are connected to the system control unit 8 via a system bus 7. The system control unit 8 controls timing of driving each of the units described above, and flow of data, etc. The system control unit 8 can be implemented by a computer that operates according to a computer program.

As described above, according to this embodiment, the breathing of a patient is guided in response to an imaging start request signal by a technologist, so that dynamic imaging of a predetermined breathing cycle is enabled only by the technologist pressing an X-ray radiation exposure request button while monitoring the patient.

Second Embodiment

Figure 4:
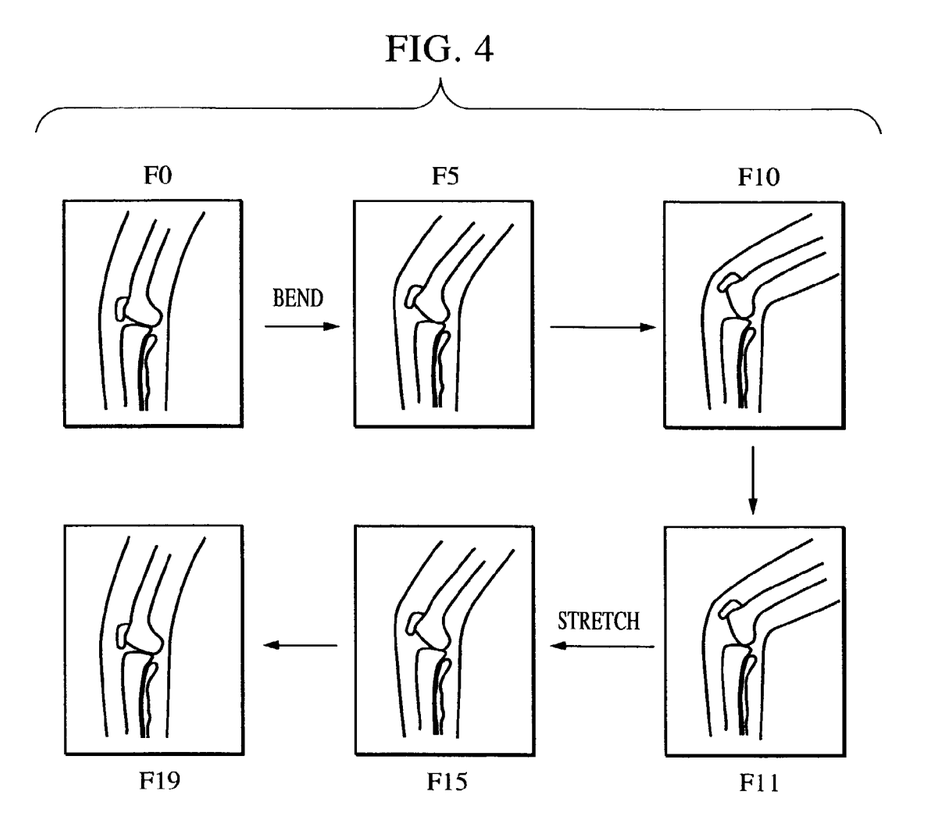
FIG. 4 is a schematic diagram showing images of the dynamic state of a knee joint in bending and stretching exercises.

Although the first embodiment has been described in the context of dynamic imaging of respiration, dynamic imaging is also effective for diagnosis of other body parts capable of motion, such as the abdomen (in abdominal respiration), the lumbar vertebrae and the extremities and the like including joints in bending and stretching motion, and the like. In dynamic imaging for these body parts, guiding of the dynamic state (moving state) of the relevant body part is also needed, since diagnosis will be difficult if the dynamic state (cycle, changing process of phase, or the like, of the dynamic state) of the body part is left up to each patient. As an example, FIG. 4 shows dynamic images of a knee joint during a bending and stretching motion. FIG. 4 shows some of twenty frames acquired by dynamic imaging of the knee joint. The knee joint is initially stretched in a state F0, and is gradually bent until reaching a state F10 or F11. Then, conversely, the knee joint is gradually stretched until reaching a state F19 in which the knee joint is fully stretched. In the case of dynamic imaging of the knee joint, indication, similar to that of FIG. 3, for guiding the phase of dynamic state is also effective. The term "phase" is used here to refer to information indicating a stage, in a series of stages of a dynamic process of at least a part of the object.

In dynamic imaging of the extremities, etc., in some cases, imaging of a plurality of cycles of dynamic state provides significant information. This is because a particular symptom does not necessarily appear clearly in one cycle of a given motion of cartilages and muscles, and the like. Thus, with consideration of the dose of radiation required for imaging, it is effective to preset the number of cycles a dynamic state to be imaged for imaging and the number of cycles of guiding the dynamic state continuously indicated after start of radiation exposure, in accordance with the particular body part to be imaged and/or the purpose of imaging, and/or the like. Thus, the number of cycles of dynamic state and/or the number of cycles of guiding dynamic state is stored in a storage unit (not shown) in the system control unit 8 as a set value that can, preferably, be selected or changed as needed.

Furthermore, the system control unit 8 stores a standard time of one cycle, which serves as a target in guiding a process such as arises through breathing, or a bending and stretching movement, or the like, in accordance with the body part(s) to be imaged and/or the purpose of imaging, and/or the like. Depending on the age, medical condition, etc., of the patient, it is possible that the standard time may be inappropriate. In such cases, it is effective to change the cycle of the guiding in accordance with the information of the particular patient to be imaged. This patient information is input from a hospital information system (abbreviated as "HIS", and described below) or a radiology department information system (abbreviated as RIS and described later) via a network, or input from an input unit 16 that serves as a user interface. The patient information includes information regarding current status and past record of diseases, etc., in addition to age and sex of the patient.

For example, it is sometimes difficult for children, aged patients or patients with respiratory disease to breathe in a standard breathing cycle. In such cases, the parameters of the breathing may be automatically changed and set to be shorter or longer than the standard cycle, in accordance with the patient information. Furthermore, a detailed examination is sometimes required for patient with a particular disease. In such cases, two cycles, instead of the usual one cycle, may be set to be imaged automatically in accordance with the patient information (it is, however, also within the scope of the invention for the number of cycles to be selected or input by the operator).

Patient information and dynamic imaging parameters such as a manner of indication for guiding dynamic state is related by a table prestored in the system control unit 8. The table also allows setting of a manner of process of change in phase of dynamic state in a cycle of the dynamic state (or a predetermined series of the dynamic state) in accordance with a body part to be imaged, patient information, and/or diagnostic purpose, etc. For example, although the durations of the inhaling period and of the exhaling period are the same in the example shown in FIG. 3, setting may be such that the inhaling period is longer and the exhaling period is shorter (i.e., exhaling in a burst), such as in the case of measuring vital capacity. As just described, it is also effective to automatically change a manner of indication for guiding dynamic state in accordance with the diagnostic purpose, etc., for a given body part to be imaged. Information including the diagnostic purpose is also input from the HIS, RIS, or the input unit 16 mentioned above.

As described above, a cycle of dynamic state or a predetermined manner of a series of dynamic state is set in accordance with the body part to be imaged, patient information, and diagnostic purpose, etc., dynamic state guiding indication is performed in accordance with the setting, and an imaging operation (X-ray pulse irradiation, capturing of image data, etc.) is executed in association with the guiding indication. For example, X-ray pulse irradiation is performed and image data is captured in accordance with the number of dynamic state cycles, or X-ray pulse irradiation is performed and image data is captured in a cycle in accordance with rate of change, in dynamic state phase, with time.

When the dynamic images captured in various manners as described above are displayed, it is sometimes needed to reflect imaging conditions (imaging operation manner). For that purpose, information relating to imaging timing and information relating to dynamic state guiding indication, etc., must be stored (for example, as header information or the like of the image data) together with the dynamic image data. The information relating to imaging timing is, for example, approximate timing of imaging (absolute or relative time, etc.), and is stored based on an internal clock of the imaging system with a resolution, for example, on the order of a millisecond. Furthermore, information regarding dynamic state guiding indication used when imaging (cycle, number of cycles, and/or manner of process of change in dynamic state phase, information regarding dynamic state phase corresponding to each indication, etc.) is also stored. For example, information regarding dynamic state phase corresponding to each indication is stored as header information in a predetermined image data format in association with each image constituting the dynamic images.

When the dynamic images that have been obtained are displayed dynamically, it is sometimes desired for diagnosis that the images be displayed on the same time scale as when the images were actually acquired. However, in some cases, it is difficult for a doctor to diagnose images on the same time scale as when the images were acquired, for example, when the dynamic imaging is of the chest in respiration with a short exhaling period. In such a case, it is effective to display images by non-linearly converting the time scale for display, relative to the time scale of the imaging, for example, to extend the time interval of display in the exhaling period regardless of the actual time interval in imaging.

Furthermore, when imaging is performed over a plurality of dynamic state cycles, images may be displayed in various methods. For example, images of the plurality of cycles may be displayed as a single sequence, the dynamic images may be divided on a cycle-by-cycle basis and dynamic images of the respective cycles are arranged spatially so as to be displayed in parallel substantially in phase with each other, or phase analysis of the dynamic images may be performed and images of the plurality of cycles may be rearranged based on the phases, obtained by the analysis, of the dynamic images and displayed like as dynamic images of one cycle. The phase analysis is executed by analyzing the image data, for example, in the case of dynamic images of the chest with respiration, by extracting a geometric feature value such as area or height of the lung region, from the image data. A method of display may be automatically selected in accordance with information of a body part to be imaged, a patient, and/or diagnostic purpose, or in accordance with every operation of the operator, from among the various display methods.

Furthermore, some patients sometimes fail to perform the action(s) necessary for imaging of the dynamic state in accordance with dynamic state guiding indication(s). This is problematic because images are obtained of which phases are different from respective dynamic state phases in the information concerning dynamic state guiding indication attached to the image data. Thus, the phase analysis described above is performed on at least part of dynamic images. If the phase that is determined by the analysis does not match the phase attached to the image data (e.g., if the difference between those phases is larger than a predetermined threshold value), the phase analysis is performed on all the dynamic images, and the phase information attached to the image data is corrected and/or the dynamic images are rearranged based on the phase information obtained by the analysis, whereby the above problem is solved. This process including the phase analysis is executed using the image processing unit 12.

Figure 5:
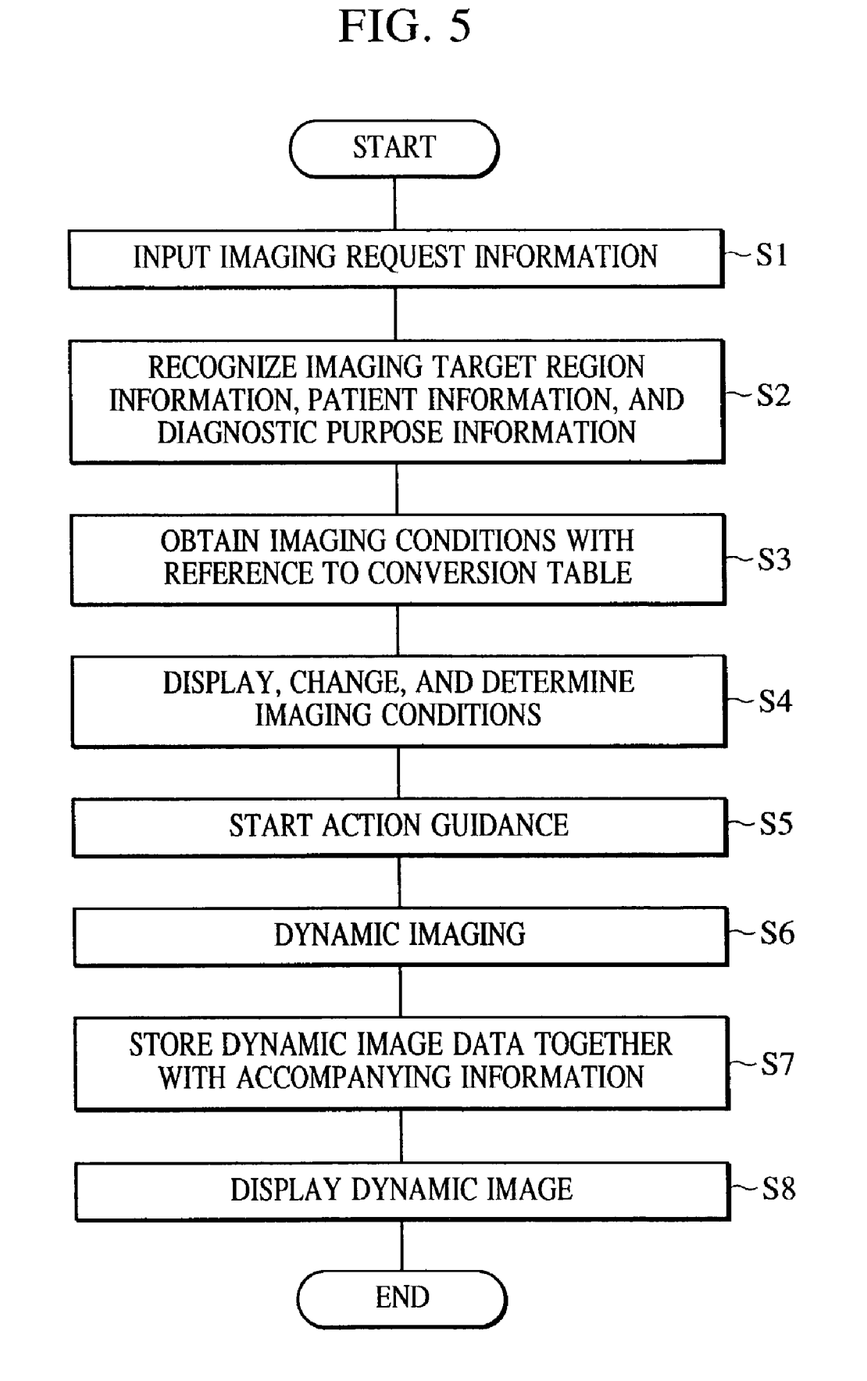
FIG. 5 is a flowchart showing operation of the system according to the embodiment.

FIG. 5 shows a flowchart of the above operation. Referring to FIG. 5, first, imaging request information is input from the hospital information system, the radiology department information system, or the input unit 16 serving as a user interface (step S1). Then, information from step S1, including at least one of patient information (information indicating the object to be imaged), body part information (information of the imaging target region), and diagnostic purpose information, is recognized (step S2). Then, imaging conditions are obtained with reference to a conversion table storing the imaging conditions (manner of dynamic state guiding indication, manner of X-ray pulse irradiation, manner of capturing image data, etc.) correspondent to the information recognized in step S2 (step S3). Then, the imaging conditions obtained in step S3, in particular, manners of dynamic state guiding indication such as a dynamic state cycle (time of dynamic state guiding indication), number of iteration of a dynamic state cycle (number of iteration of dynamic state guiding indication), and manner of change in dynamic state phase in a dynamic state cycle (manner of process in the dynamic state guiding indication), and the like, are displayed, allowed to be changed as needed, and fixed by a predetermined operation such as an operation for instructing start of imaging (step S4). Then, in response to an operation for instructing start of imaging by an operator, guiding indication in accordance with the manner of dynamic state guiding indication determined in step S4 is started (step S5). Then, in response to an operation for instructing radiation exposure by an operator, dynamic imaging is performed in association with the dynamic state guiding indication (step S6). Image data obtained by dynamic imaging in step S6 is stored with information of an imaged body part, patient information, diagnostic purpose information, information concerning imaging timing, information concerning dynamic state guiding indication, and the like, attached (step S7). Then, dynamic images based on the image data stored in step S7 are dynamically displayed in a display method in accordance with the attached information (step S8).

Features of the first and second embodiments may be combined as may be suitable.

Other Embodiments

It is to be understood that the object of the present invention can also be achieved by supplying a storage medium storing program code of software for implementing the functions of the apparatus or system according to the first or second embodiment (or a combination of functions from both) to an apparatus or system so that a computer (CPU, MPU, etc.) of the apparatus or system reads and executes the program code stored in the storage medium.

In that case, the program code itself, read from the storage medium, achieves the functions of the first or second embodiment (or combination), and thus the storage medium storing the program code and the program code itself constitute an embodiment of the present invention.

The storage medium for providing the program code may be, for example, a ROM, a floppy (registered trademark) disk, a hard disk, an optical disk, a magneto-optical disk, a CD-ROM, a CD-R, a magnetic tape, a non-volatile memory card, etc.

Furthermore, not only by the computer reading and executing the program code, but also by the computer executing part of or the entire process utilizing an OS, etc. running on the computer based on instructions of the program code, the functions of the first or second embodiment (or a combination of both) may be achieved. The latter is also one of embodiments of the present invention.

Furthermore, the program code read from the storage medium may be written to a memory of a function extension board inserted in the computer or a function extension unit connected to the computer. The functions of the first or second embodiment (or a combination) may be realized by executing part of or the entire process by a CPU, etc., of the function extension board or the function extension unit based on instructions of the program code. This is also one of the embodiments of the present invention.

When the present invention is applied to a program or a storage medium storing the program, the program includes, for example, program code corresponding to the flowchart shown in FIG. 5 and described above.

Figure 6:
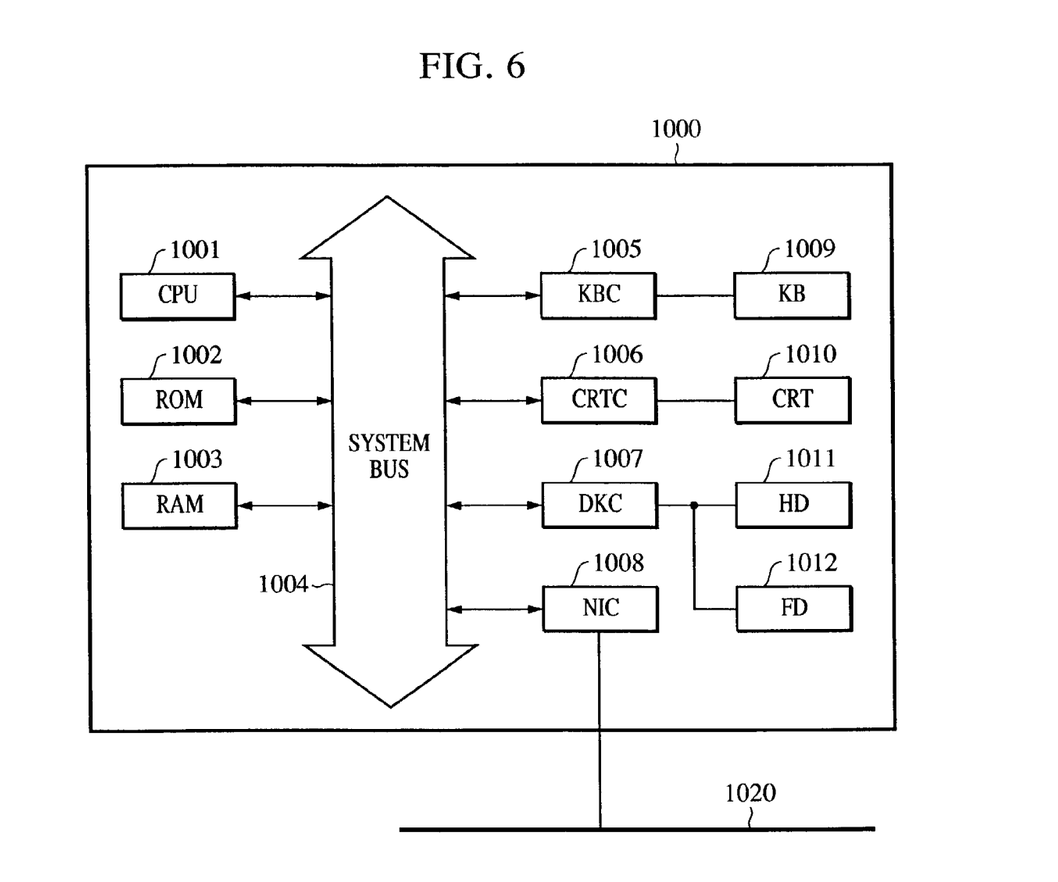
FIG. 6 is a block diagram of a computer that is capable of executing a program associated with a function or operation of the embodiment.

FIG. 6 shows the constitution of the computer 1000 described above.

As shown in FIG. 6, the computer 1000 includes a CPU 1001, a ROM 1002, a RAM 1003, a keyboard controller (KBC) 1005 for performing control concerning a keyboard (KB) 1009, a CRT controller (CRTC) 1006 for performing control concerning a CRT display (CRT) 1010 that functions as a display unit, a disk controller 1007 for performing control concerning a hard disk (HD) 1011 and a floppy (registered trademark) disk (FD) 1012, and a network interface controller (NIC) 1008 for connection with a network 1020, these components being connected to one another via a system bus 1004 so that communications thereamong are enabled.

The CPU 1001 synthetically controls the components connected to the system bus 1004 by executing programs stored in the ROM 1002 or the HD 1011 or supplied from the FD 1012.

That is, the CPU 1001 executes control so as to achieve operations of the embodiments described above by reading processing programs according to a predetermined processing sequence from the ROM 1002, the HD 1011, or the FD 1012.

The RAM 1003 functions as a main memory or work area of the CPU 1001 or the like. The KBC 1005 executes control associated with input of indications from the KB 1009, a pointing device that is not shown, etc. The CRTC 1006 executes control regarding display on the CRT 1010.

The DKC 1007 executes control pertaining to access to the HD 1011 and FD 1012, in which a boot program, various application programs, editing files, user files, network management programs, and given predetermined processing programs, and the like, are stored.

The NIC 1008 exchanges data or the like bidirectionally with apparatuses or systems on the network 1020.

It is to be understood that the present invention may also be applied to a system including a plurality of apparatuses (e.g., radiation generating apparatuses, radiographic apparatuses, image processing apparatuses, and interface apparatuses, etc.) and to a single apparatus in which functions of these apparatuses are integrated. When the present invention is applied to a system including a plurality of apparatuses, the apparatuses are connected with one another via, for example, an electric connecting device (communication device), an optical connecting device (communication device), and/or a mechanical connecting device, and/or the like.

Figure 7:
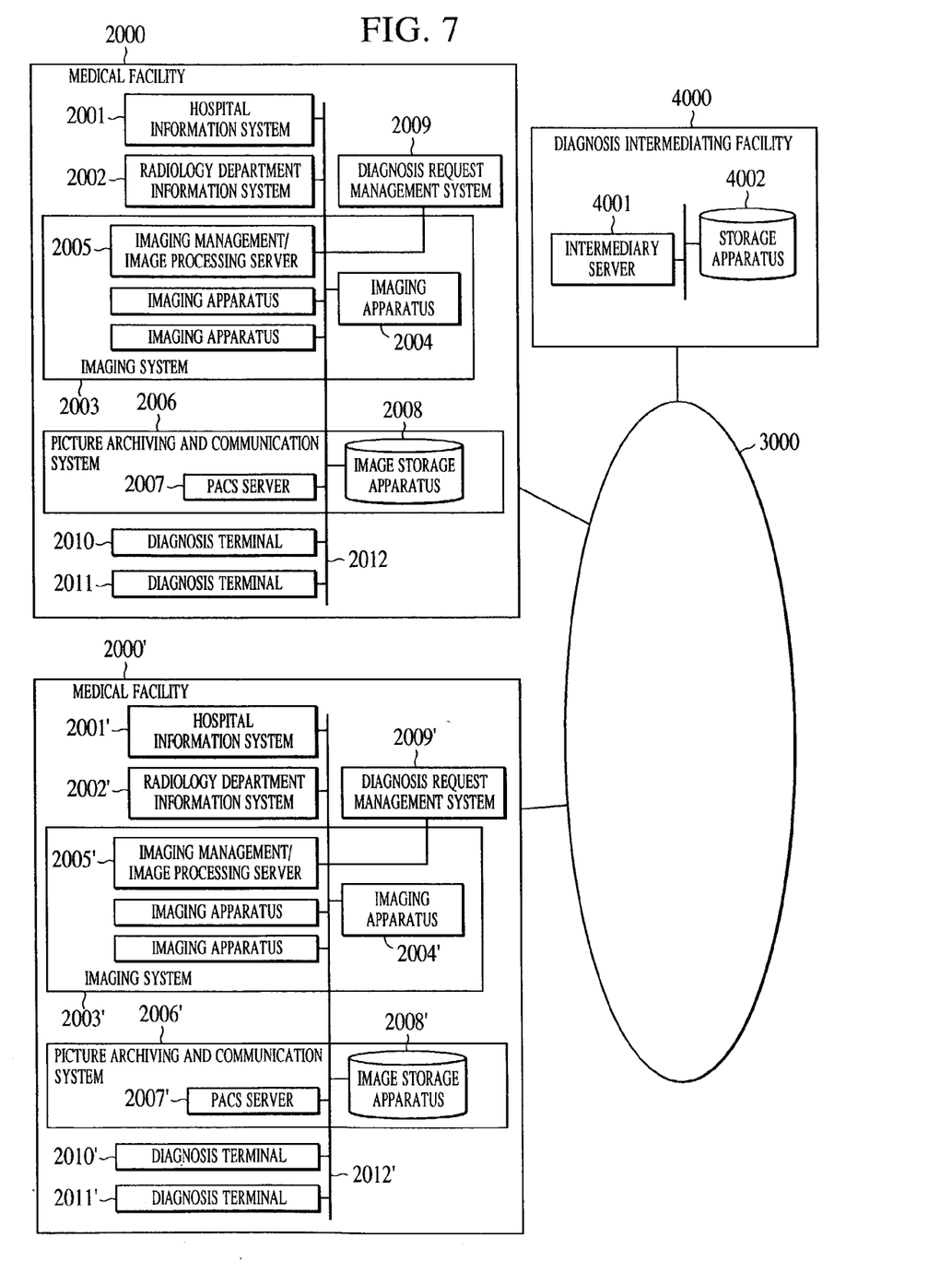
FIG. 7 is a diagram showing a system or group of medical facilities, constituted using a network connection, to which the present invention is applied.

Furthermore, the present invention may also be applied to an image diagnosis aiding system including a network (LAN and/or WAN, etc.) shown in FIG. 7. Referring to FIG. 7, information regarding a patient that has come to a medical facility 2000 (e.g., carte information (data in the medical records or patient's file), examination information, accounting information, etc.) is managed by a hospital information system (hereinafter abbreviated as HIS) 2001 including a computer or computer network, etc. A radiology department information system (hereinafter referred to as RIS) 2002 including a computer or computer network, etc., manages information in a radiology department, and for example, it manages a radiography request information from the HIS in cooperation with an imaging system (radiographic system) 2003 to be described later.

The imaging system 2003 is used for radiography, and it includes, for example, at least one imaging apparatus 2004 for radiographing a patient and outputting image data, and an imaging management/image processing server 2005 for management of radiographing based on radiography request information from the RIS, etc., and/or image processing of radiographs, etc. The imaging system 2003 or the imaging apparatus 2004 includes, for example, the system shown in FIG. 1 described above.

A picture archiving and communication system (hereinafter abbreviated as PACS) 2006 includes, as a function, archiving image data from the imaging system 2003 together with information required for management of the image data and/or image diagnosis, etc. (also referred to as attached information), and providing the image data (and the attached information) as needed. The PACS 2006 includes, for example, a PACS server 2007 including a computer or computer network, and an image storage apparatus 2008 for storing the image data and the attached information.

A diagnosis requesting and management system 2009 operates in cooperation with the imaging system 2003 and/or the PACS 2006, etc., transmitting diagnosis request information for image data acquired by the imaging system 2003 to a diagnostician automatically or based on an operation by an operator (e.g., radiological technologist) so as to serve the image data to image diagnosis (image interpretation by the diagnostician), and executing management of progress of image diagnosis, etc. The diagnosis requesting and management system 2009 includes a computer or computer network, etc.

Diagnosis terminals (image viewers, etc.) 2010 and 2011 are used by diagnosticians, and each of the diagnosis terminals 2010 and 2011 includes a computer or computer network, etc., that is capable of, for example, receiving diagnosis request information from the diagnosis requesting and management system 2009, retrieving image data and attached information from the PACS 2006, inputting diagnostic result by a diagnostician, transmitting information indicating the result of diagnosis and/or completion of diagnosis to the diagnosis requesting and management system 2009, etc.

The above components 2001 to 2011 are connected with one another via a LAN (local area network) 2012. The diagnostic result information is transmitted from the diagnosis requesting and management system 2009 or directly from the diagnosis terminals 2010 and 2011 to at least one of the hospital information system 2001, the radiology department information system 2002, and the PACS 2006.

Destination of the diagnosis request from the diagnosis requesting and management system 2009 is not limited to that within the medical facility 2000. For example, diagnosis may be requested to a diagnostician of another medical facility via a WAN (wide area network) utilizing a public line or a private line. FIG. 7 is shows an example where the medical facility 2000 is connected to another medical facility 2000' via the Internet 3000. The medical facility 2000' herein includes, without limitation, components 2001' to 2012' similarly to those of the medical facility 2000. The diagnosis requesting and management system 2009 of the medical facility 2000 is capable of requesting diagnosis to, for example, the medical facility 2000' via the Internet 3000 and the diagnosis requesting and management system 2009' of the medical facility 2000', and obtaining the result of the diagnosis therefrom.

Furthermore, instead of a system in which diagnosis request information, image data, and diagnosis result information are directly exchanged among medical facilities, a system including a diagnosis intermediating facility 4000 may be implemented. In that case, for example, the diagnosis requesting and management system 2009 of the medical facility 2000 transmits diagnosis request information including image data to the diagnosis intermediating facility 4000 via the Internet 3000. The diagnosis intermediating facility 4000 is owned by a diagnosis intermediating service agency (diagnosis intermediating service company, etc.), and it includes an intermediary server 4001 including a computer or computer network, and a storage apparatus 4002 that stores data as needed.

The intermediary server 4001 have the functions of selecting a medical facility and/or a diagnostician that is suitable for diagnosis based on the diagnosis request information from the medical facility 2000, transmitting the diagnosis request information to the selected medical facility and/or diagnostician, providing image data, etc., as needed, to the medical facility and/or diagnostician, obtaining diagnosis result information from the medical facility and/or the diagnostician, providing the diagnosis result information and other relevant information to the medical facility 2000, and so forth. The storage apparatus 4002 stores, in addition to the diagnosis request information, data required for executing the above functions, such as data required for selecting a medical facility and/or a diagnostician suitable for diagnosis (e.g., data concerning network address, field of diagnostic ability, diagnostic skill, schedule, etc. of the medical facility and/or the diagnostician). According to the system configuration, the diagnosis requesting and management system 2009 of the medical facility 2000 is allowed to receive diagnosis result information from a medical facility and/or a diagnostician that is suitable for diagnosis via the Internet 3000 and the diagnosis intermediating facility 4000.

The medical facility 2000 is not limited to being a hospital, and may be, for example, a medical examination and diagnosis clinic where a diagnostician works, in which case the medical facility 2000 is replaced by a medical examination and diagnosis clinic (not shown) including components similar to the components 2003 to 2012. Furthermore, the medical facility 2000 may be a medical examination clinic where only medical examination (e.g., radiography) is performed. In that case, for example, the medical facility 2000 is replaced by a medical examination clinic (not shown) including components similar to the components 2003 to 2009 and 2012.

Furthermore, part of the systems, apparatuses, units, or the functions in the medical facility 2000 (e.g., the image processing unit 12 or part of the functions thereof in the imaging system 2003 or the imaging apparatus 2004) may reside outside the medical facility 2000, and may be replaced, for example, by similar systems, apparatuses, units, or functions in other facilities via the Internet 3000.

Now, a procedure of processing by the imaging system 2003 and the diagnosis requesting and management system 2009 in the medical facility 2000 will be described. First, a procedure of processing executed by the imaging system 2003 will be described with reference to a flowchart shown in FIG. 8. First, in step S5001, the imaging system 2003 determines whether any imaging request information has been transmitted from the HIS or RIS. If any imaging request information is found, the imaging system 2003 proceeds to step S5003 whereas it proceeds to step S5002 if no imaging request information is found. In step S5002, the imaging system 2003 determines whether an exit instruction has been issued thereto. If an exit instruction has been issued, the imaging system 2003 exits processing. If no exit instruction has been issued, the imaging system 2003 returns to step S5001 to continue processing. In step S5003, the imaging system 2003 executes imaging as in the embodiments described earlier.

Figure 8:
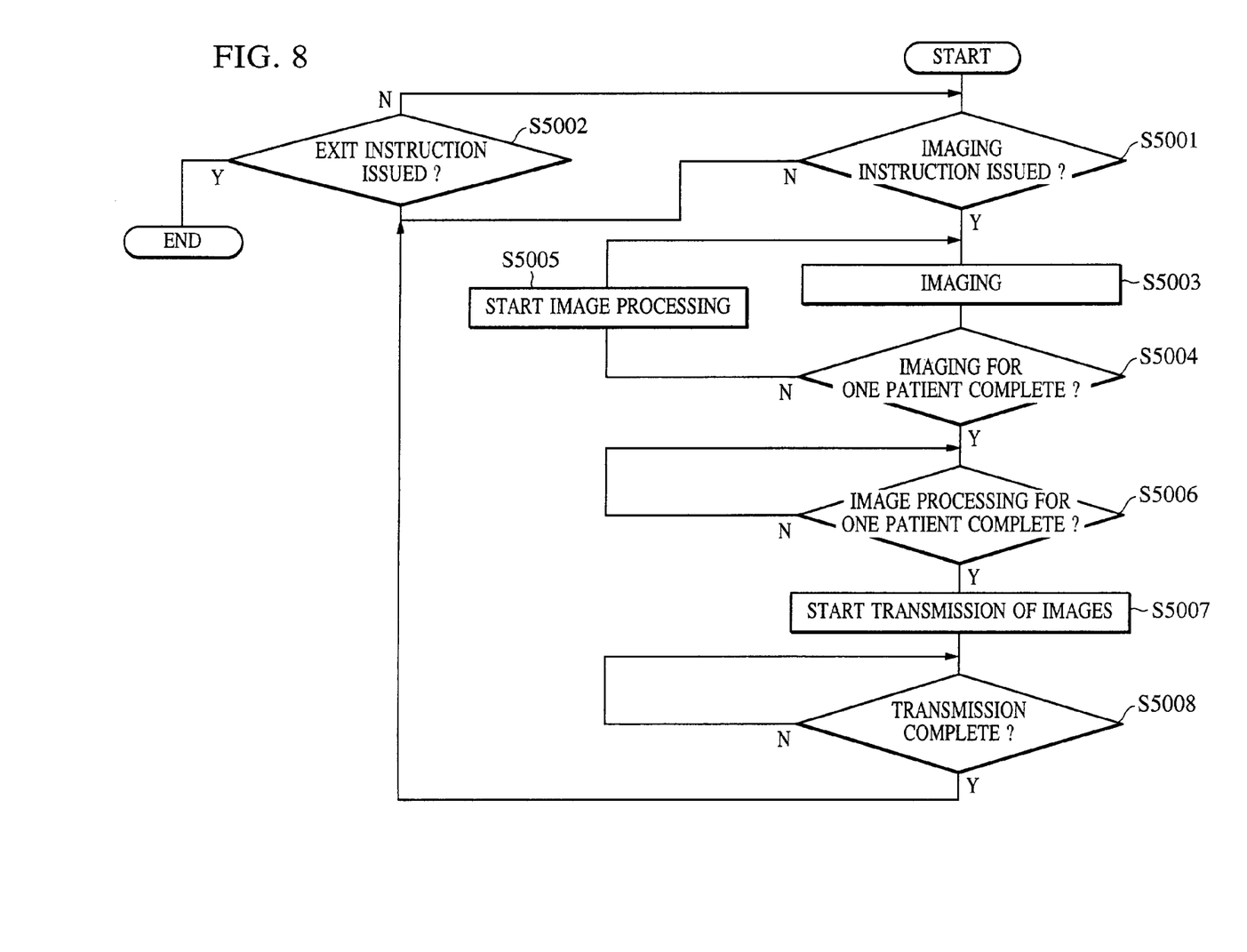
FIG. 8 is a flowchart showing a procedure of processing by an imaging system.

After execution of imaging, the imaging system 2003 determines whether all the imaging requested for one patient is completed (step S5004). If imaging is not completed, the imaging system 2003 starts image processing of a radiograph acquired by previous imaging in step S5005, and returns to step S5003 to continue imaging process. At this time, the image processing is executed as in the embodiments described earlier, and in parallel with the imaging process in step S5003. When imaging is completed for the patient, the imaging system 2003 proceeds to step S5006.

In step S5006, the imaging system 2003 determines whether image processing of all the images of the patient, acquired by imaging, is complete. If image processing for all the images is completed, the imaging system 2003 proceeds to step S5007. If the image processing is not complete, the determination in step S5006 is repeated.

In step S5007, the imaging system 2003 starts transmission of all the image data, of the patient, that have been processed. For example, all the image data is transmitted to the PACS 2006, and data for accessing the image data transmitted to the PACS 2006 is transmitted to the diagnosis requesting and management system 2009.

In step S5008, the imaging system 2003 determines whether transmission of the image data is complete. If the transmission is completed, the imaging system 2003 proceeds to step S5002. If the transmission is not completed, the determination in step S5008 is repeated.

Figure 9:
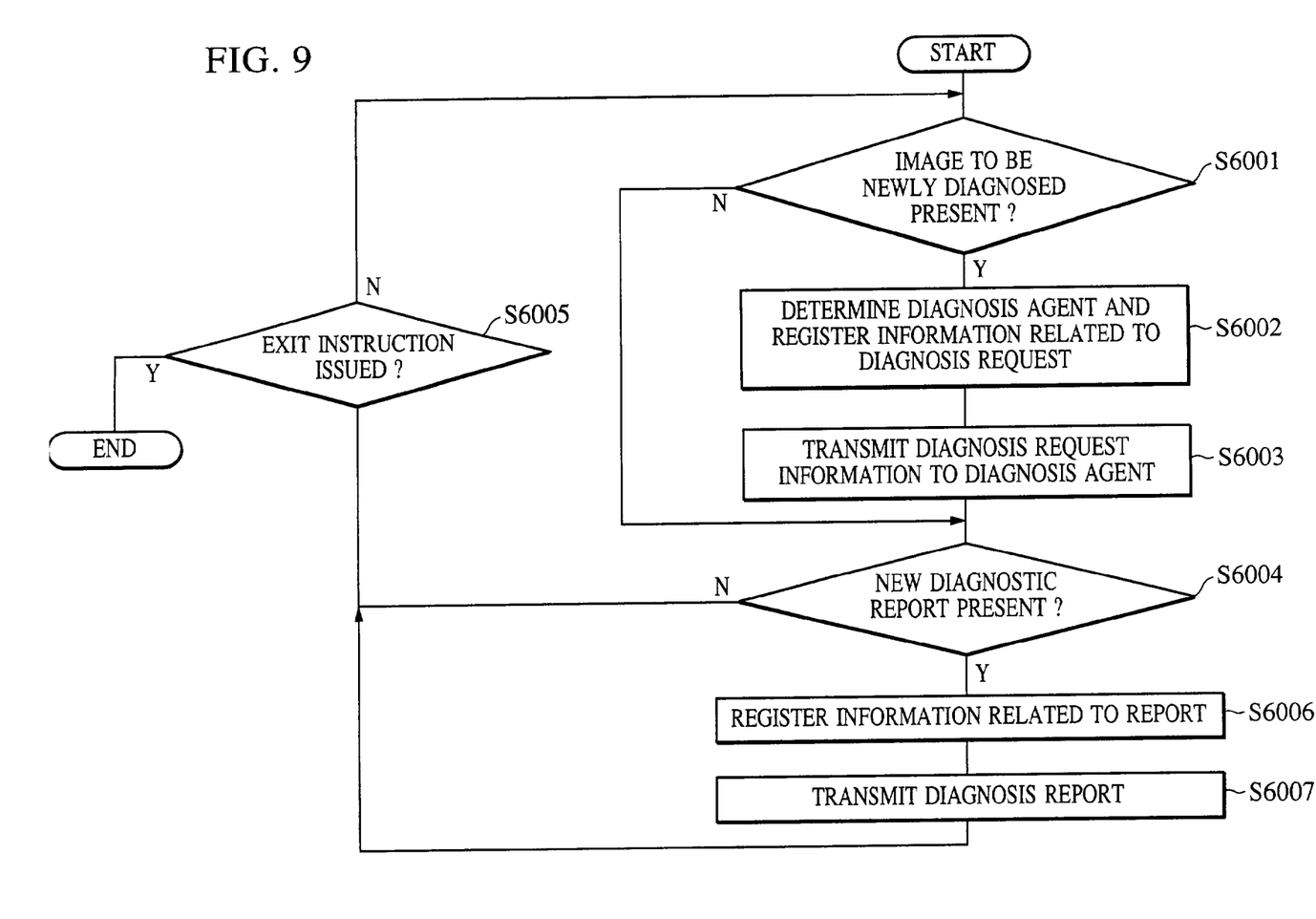
FIG. 9 is a flowchart showing a procedure of processing by a diagnosis requesting and management system.

Next, a procedure of processing by the diagnosis requesting and management system 2009 will be described with reference to a flowchart shown in FIG. 9. First, in step S6001, whether radiographic image data for each patient for which diagnosis request is to be requested is present is determined. The determination is made based on information regarding radiographic image data for each patient, transmitted from the imaging system 2003, the medical facility 2000', or the diagnosis intermediating facility 4000, etc., for example, information for accessing image data transmitted to PACS, etc. If the image data is present, the diagnosis requesting and management system 2009 proceeds to step S6002, whereas it proceeds to step S6004 if the image data is not present.

In step S6002, a destination of diagnosis request for images for which diagnosis is to be requested is determined. Furthermore, in order to manage progress of diagnosis, information concerning diagnosis request including information of the destination of diagnosis request is registered in a storage unit. The destination is determined based on information concerning the images, for example, information stored in the storage unit, as header information of the image data, etc., associated with the images (e.g., body part to be imaged of a patient, imaging method, diagnostic purpose, disease information, diagnostician designation information, etc.). The destination may be, as described above, the medical facility 2000' or the diagnosis intermediating facility 4000. Then, in step S6003, the diagnosis request information including information for identifying images to be diagnosed or image data to be diagnosed is transmitted to the destination that has been determined.

Then, in step S6004, it is determined whether any new diagnosis report is present. The determination is made based on information received from the diagnosis terminal 2010 or 2011, the medical facility 2000', or the diagnosis intermediating facility 4000, etc. If any new diagnosis report is present, the diagnosis requesting and management system 2009 proceeds to step S6006, whereas it proceeds to step S6005 if no new diagnosis report is present. In step S6005, it is determined whether an exit instruction has been issued to the diagnosis requesting and management system 2009. If an exit instruction has been issued, the diagnosis requesting and management system 2009 exits the procedure. If no exit instruction has been issued, the diagnosis requesting and management system 2009 returns to step S6001 to continue operation.

In step S6006, as part of diagnosis progress management, information regarding a diagnostic report (acquisition date, report content, etc.) is registered in the storage unit. Then, in step S6007, the diagnosis report is transmitted (forwarded) to a predetermined destination such as the HIS 2001, the RIS 2002, the PACS 2006, or the origin of the diagnosis request (such as the medical facility 2000' or the diagnosis intermediating facility 4000, etc.). Then, the diagnosis requesting and management system 2009 proceeds to the determination in step S6005 described earlier.

Although the diagnosis requesting and management system 2009 has been described as implemented by a dedicated computer, without limitation thereto, it may be functionally incorporated into the HIS 2001, the RIS 2002, the imaging management/image processing server 2005 in the imaging system 2003, the PACS server 2007 in the PACS 2006, etc.

As described hereinabove, the present invention achieves the object described earlier.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A radiographic apparatus for imaging a dynamic state of a human body, comprising:
   an X-ray generating means for generating an X-ray;
   a first indication means for guiding the human to perform cyclical movement with a dynamic state guiding indication using a perceivable pattern which is repeated with a predetermined timing;
   an image acquisition means for acquiring X-ray image data constituting a plurality of X-ray images of the human body;
   a control means for synchronizing said image acquisition with the dynamic state guiding indication and attaching to each of the images information representing dynamic state phase based on the dynamic state guiding indication;
   a storage means for storing the number of cycles of dynamic state and/or number of cycles of guiding dynamic state;
   a phase analysis means for analyzing the image data by extracting a measurement of an anatomical feature in the image data;
   a determination means for determining if an analyzed phase of at least part of dynamic images matches the respective dynamic state phase in the information concerning dynamic state guiding indication attached to the image data;

a modification means for correcting the phase information attached to the image data and/or rearranging the dynamic images based on the phase information obtained by the analysis of all the dynamic images, if the determination means concludes the phases do not match; and a second indication means for displaying dynamic images based on the image data using a display method in accordance with the attached information.

2. An apparatus according to claim 1, wherein said storage means further stores a standard time of one cycle in accordance with the body part(s) to be imaged and/or the purpose of imaging.

3. An apparatus according to claim 1, wherein the measure of a feature in the image date is the area or height of the lung region of the human body in the case of dynamic images of the chest with respiration.

4. An apparatus according to claim 1, wherein said determination means determines whether the difference between a phase determined by the phase analysis unit and the phase attached to the image data is larger than a predetermined threshold value or not.

5. A radiographic method of imaging a dynamic state of a human body by a radiographic apparatus, including an image acquisition unit adapted to acquire a radiograph, said radiographic method comprising:

an X-ray generating step, for generating an X-ray;

a first indication step, for guiding the human to perform a cyclical movement with a dynamic state guiding indication using a perceivable pattern which is repeated with a predetermined timing;

an image acquisition step, for acquiring X-ray image data constituting a plurality of X-ray images of the human body;

a control step, for synchronizing said image acquisition with the dynamic state guiding indication and attaching to each of the images information representing dynamic state phase based on the dynamic state guiding indication;

a storage step, for storing the number of cycles of dynamic state and/or the number of cycles of guiding dynamic state;

a phase analysis step, for analyzing the image data by extracting a measurement of an anatomical feature in the image data;

a determination step, for determining if an analyzed phase of at least part of dynamic images matches the respective dynamic state phase in the information concerning dynamic state guiding indication attached to the image data;

a modification step, for correcting the phase information attached to the image data and/or rearranging the dynamic images based on the phase information obtained by the analysis of all the dynamic images, if the determination step concludes the phases do not match; and a second indication step, for displaying dynamic images based on the image data using a display method in accordance with the attached information.

6. A computer-readable storage medium storing a program for having a computer execute a method of imaging a dynamic state of a human body by a radiographic apparatus including an image acquisition unit for acquiring a radiograph, said method comprising:

an X-ray generating step, for generating an X-ray;

a first indication step, for guiding the human to perform cyclical movement with a dynamic state guiding indication using a perceivable pattern which is repeated with a predetermined timing;

an image acquisition step, for acquiring X-ray image data constituting a plurality of X-ray images of the human body;

a control step, for synchronizing said image acquisition with the dynamic state guiding indication and attaching to each of the images information representing dynamic state phase based on the dynamic state guiding indication;

a storage step, for storing the number of cycles of dynamic state and/or the number of cycles of guiding dynamic state;

a phase analysis step, for analyzing the image data by extracting a measurement of an anatomical feature in the image data;

a determination step, for determining if an analyzed phase of at least part of dynamic images matches the respective dynamic state phase in the information concerning dynamic state guiding indication attached to the image data;

a modification step, for correcting the phase information attached to the image data and/or rearranging the dynamic images based on the phase information obtained by the analysis of all the dynamic images, if the determination step concludes the phases do not match; and a second indication step, for displaying dynamic images based on the image data using a display method in accordance with the attached information.

* * * * *

UNITED STATES PATENT AND TRADEMARK OFFICE
CERTIFICATE OF CORRECTION

| | | |
|---|---|---|
| PATENT NO. | : 7,050,537 B2 | Page 1 of 1 |
| APPLICATION NO. | : 10/290184 | |
| DATED | : May 23, 2006 | |
| INVENTOR(S) | : Osamu Tsujii | |

It is certified that error appears in the above-identified patent and that said Letters Patent is hereby corrected as shown below:

<u>COLUMN 15</u>:

Line 15, "date" should read --data--.

Signed and Sealed this

Fifth Day of June, 2007

JON W. DUDAS
*Director of the United States Patent and Trademark Office*